United States Patent
Hong et al.

(10) Patent No.: US 10,093,677 B2
(45) Date of Patent: Oct. 9, 2018

(54) METHOD FOR PREPARING SPIRO QUATERNARY AMMONIUM SALT

(71) Applicant: SAMHWA PAINTS INDUSTRIES CO., LTD., Ansan-si, Gyeonggi-do (KR)

(72) Inventors: Myeng Chan Hong, Pyeongtaek-si (KR); Young Seop Choi, Ansan-si (KR); Seung Hun Lee, Yonginsi (KR); Da Eun Kwon, Gunpo-si (KR); So Hyun Jang, Ansan-si (KR); June Hyeop An, Ansan-si (KR); Chong Yun Kwag, Jongno-gu (KR)

(73) Assignee: SAMHWA PAINTS INDUSTRIES CO., LTD., Ansan-Si, Gyeonggi-Do (KR)

( * ) Notice: Subject to any disclaimer, the term of this patent is extended or adjusted under 35 U.S.C. 154(b) by 0 days.

(21) Appl. No.: 15/490,629

(22) Filed: Apr. 18, 2017

(65) Prior Publication Data

US 2018/0186804 A1 Jul. 5, 2018

(30) Foreign Application Priority Data

Jan. 4, 2017 (KR) .................. 10-2017-0001365

(51) Int. Cl.
C08F 8/44 (2006.01)
C07D 487/10 (2006.01)
B01J 41/14 (2006.01)

(52) U.S. Cl.
CPC ............ *C07D 487/10* (2013.01); *B01J 41/14* (2013.01); *C08F 8/44* (2013.01)

(58) Field of Classification Search
None
See application file for complete search history.

(56) References Cited

U.S. PATENT DOCUMENTS

| 6,271,264 B1* | 8/2001 | Dhal .................... A61K 31/787 |
| | | 424/78.01 |
| 6,365,705 B1* | 4/2002 | Leon ......................... C08F 8/44 |
| | | 528/271 |
| 6,980,415 B2 | 12/2005 | Higono |
| 2005/0219798 A1* | 10/2005 | Higono .................. H01G 9/038 |
| | | 361/504 |
| 2007/0247472 A1* | 10/2007 | Tong ..................... G01L 311/24 |
| | | 345/582 |

FOREIGN PATENT DOCUMENTS

| CN | 104277045 A | 1/2015 |
| CN | 104387397 A | 3/2015 |
| WO | 2007/027649 A1 | 8/2007 |

OTHER PUBLICATIONS

Blicke et al., "Polycyclic Quaternary Ammonium Salts. III", J Am Chem Soc 76(20) 5099-5103 (1954).
Higashiya et al., "Synthessi of Oxygen-Containing Spirobipyrrolidinium Salts for High Conductivity Room Temperature Ionic Liquids", Helvetica Chimica Acta 92(8) 1600-1609 (2009).
Ue et al., "Electrochemical Properties of Organic Liquid Electrolytes Based on Quatemary Onium Salts for Electrical Double-Layer Capacitors", J Electrochem Soc 141(11) 2989-2996 (1994).

* cited by examiner

*Primary Examiner* — Robert C Boyle
(74) *Attorney, Agent, or Firm* — Nixon Peabody LLP; David S. Resnick

(57) ABSTRACT

The present invention relates to a method for preparing a spiro quaternary ammonium salt comprising reacting a cyclic secondary amine with a dihaloalkane in the presence of a basic resin. According to the preparation method of the present invention, a metal salt and halide ion are removed by filtration without any additional purification process, the spiro ammonium derivative compound can be obtained with high yield, and the resin can be reused through a simple treatment process.

10 Claims, No Drawings

METHOD FOR PREPARING SPIRO QUATERNARY AMMONIUM SALT

CROSS-REFERENCE TO RELATED APPLICATION

This application claims benefit under one or more of 35 U.S.C. § 119(a)-119(d) and (f) of Korean Patent Application No. 10-2017-0001365 filed on Jan. 4, 2017 with the Korean Intellectual Property Office, the disclosure of which is incorporated herein by reference in its entirety.

BACKGROUND

1. Field of Invention

The invention relates to a method for preparing a spiro quaternary ammonium salt in a non-aqueous electrolytic solution used for a supercapacitor, and more particularly, to a method for preparing a spiro quaternary ammonium salt comprising reacting a cyclic secondary amine with a dihaloalkane in the presence of a basic resin.

2. Description of Related Art

A supercapacitor, referred to as an electric double-layer capacitor, is a storage battery capable of being rapidly charged and discharged. The supercapacitor is frequently used as an energy storage device for high power density, long cycle life, stability and the like. Important characteristics of the supercapacitor are output characteristics, high temperature reliability, maximum operating voltage, and the like. For the supercapacitor, as the conductivity of the electrolyte is larger, the output characteristics are improved, and withstand voltage characteristics of the electrolyte affect the maximum operating voltage.

Makoto Ue et al. disclosed that a spiro quaternary ammonium salt is an electrolyte for an electrical double-layer capacitor, and shows a wide stable potential window and resistance to hydrolysis. (see, Ue, M., et al., J. Electrochem Soc. 1994, 141, 2989-2996). Among various spiro quaternary ammonium salts, spirobipyrrolidinium tetrafluoroborate exhibited the highest electrical conductivity.

Generally, spio-bipyrrolidinium tetrafluoroborate is produced by reacting a cyclic secondary amine with 1,4-dihalobutane in the presence of a metal base to synthesize a spirobipyrrolidinium halide, and then reacting it with an alkali metal tetrafluoroborate or tetrafluoroboric acid to perform an anion substitution reaction (see, Blicke, F. F.; Hotelling, E. B., Journal of American Chemical Society, 1954, 76(20), 5099-5013; and Higashiya, S., et al, Helvetica Chimica Acta, 2009, Vol 92 Issue 8, 1600-1609).

Japanese Patent Registration No. 4,371,882 discloses that pyrrolidine and 1,4-dichlorobutane are refluxed in the presence of potassium carbonate for 6 hours, and potassium chloride as a by-product is filtered to synthesize spirobipyrrrolidinium chloride, and then reacted with tetrafluoroboric acid in water solvent for 30 minutes to perform an anion substitution reaction. However, there is a disadvantage that this method requires a removal of byproducts such as potassium chloride and hydrochloric acid.

WO 2007/027649A1 discloses that pyrrolidine and 1,4-dichlorobutane are refluxed in an acetonitrile solvent in the presence of potassium chloride for 6 hours to synthesize spirobipyrrolidinium chloride, and potassium tetrafluoroborate is used in an anion substitution reaction. In addition, pyrrolidine, 1,4-dichlorobutane, potassium carbonate and potassium tetrafluoroborate are reacted at once to obtain a product. However, there are disadvantages that a recrystallization process requiring a long time, ex-pensive filtration, dialysis and reverse osmosis methods must be used to remove the by-product potassium chloride.

Chinese Patent Publication No. 104387397A discloses that the reaction is carried out by using alkali metal, tetraflororoboric acid, dihaloalkane, and cyclic amine. But, there is a problem that, in order to remove metal ions, expensive 12-crown-4 is used.

Chinese Patent Publication No. 104387397A discloses that the reaction is carried out using a cyclic amine and 1,4-butanediol, but there is a disadvantage in that strong acid and expensive palladium catalyst are used.

Chinese Patent Publication No. 104277045A discloses that the reaction is carried out using 1,4-dichlorobutane, pyrrolidine, alkali metal in the presence of sodium iodide as a catalyst. However, this method has a disadvantage in that it is necessary to remove salts generated as a by-product.

The electrolytes used for the supercapacitor require a strict limitation on the content of metal and halogen elements.

SUMMARY OF THE INVENTION

In view of the above, the present inventors have conducted intensive studies to improve disadvantages that it is necessary to remove metal and halogen anion generated as byproducts in a conventional reaction. As a result, the inventors have developed a process using a basic resin whereby water is produced as a byproduct, and the anion is adsorbed on the resin, so that a desired product can be obtained by a simple filtration. Therefore, it is an object of the present invention to provide a method for preparing a spiro quaternary ammonium compound with high purity.

Specifically, the present invention provides a method for preparing a spiro quaternary ammonium compound comprising a first step of reacting a cyclic secondary amine derivative with dihaloalkane in the presence of a basic resin, a second step of reacting the resin obtained in the first step 1 with an acid, and a third step of reacting a spiro derivative compound obtained in the first step with the resin obtained in the second step.

Also, the present invention relates to a method for preparing a spiro quaternary ammonium compound and reusing the resin, wherein the basic resin of the first step is represented by the chemical formula 1 below:

[Chemical Formula 1]

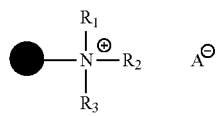

wherein $R_1$, $R_2$ and $R_3$ are each independently hydrogen or $C_1$-$C_6$ alkyl group; and anion A represents hydroxide (OH) or carbonate anion ($HCO_3^-$).

Moreover, the present invention relates to a method for preparing a spiro quaternary ammonium compound, wherein the resin obtained in the second step is represented by the chemical formula 2 below:

[Chemical Formula 2]

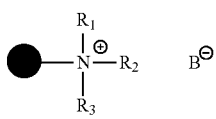

wherein $R_1$, $R_2$, and $R_3$ are each independently hydrogen or $C_1$-$C_6$ alkyl group; and anion B represents tetrafluoroborate($BF_4^-$), hexafluorophosphate($PF_6^-$), or bis(trifluoromethylsulfonyl) imide(($CF_3SO_2$)$_2N^-$).

Further, the present invention relates to a method for preparing a spiro quaternary ammonium compound, wherein the cyclic secondary amine derivative of the first step is represented by the chemical formula 3 below:

[Chemical Formula 3]

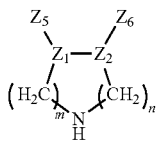

wherein m and n are independently an integer of 0 to 6; $Z_1$ and $Z_2$ are each independently CH, $CH_2$, NH, O or S; and $Z_5$ and $Z_6$ are each independently $C_1$-$C_6$ alkyl group, $C_1$-$C_6$ alkoxy group, $C_1$-$C_6$ alkenyl group, hydrogen or F.

Further, the present invention relates to a method for preparing a spiro quaternary ammonium compound, wherein the dihaloalkane of the first step is represented by the chemical formula 4 below:

[Chemical Formula 4]

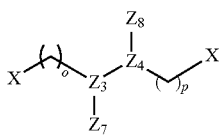

wherein o and p are each independently an integer of 0 to 6; $Z_3$ and $Z_4$ are each independently CH, $CH_2$, NH, O or S; $Z_7$ and $Z_8$ are each independently $C_1$-$C_6$ alkyl group, $C_1$-$C_6$ alkoxy group, $C_1$-$C_6$ alkenyl group, hydrogen or F; and X is Cl, Br, or I.

Further, the present invention relates to a method for preparing a spiro quaternary ammonium compound, wherein the spiro derivative compound obtained in the first step is represented by the chemical formula 5 below:

[Chemical Formula 5]

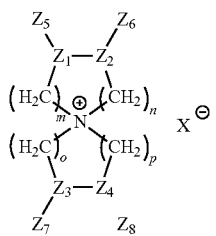

wherein m, n, o, and p are each independently an integer of 0 to 6; $Z_1$, $Z_2$, $Z_3$ and $Z_4$ are each independently CH, $CH_2$, NH, O, or S; $Z_5$, $Z_6$, $Z_7$ and $Z_8$ are each independently $C_1$-$C_6$ alkyl group, $C_1$-$C_6$ alkoxy group, $C_1$-$C_6$ alkenyl group, hydrogen or F; and X is Cl, Br, or I.

Further, the present invention relates to a method for preparing a spiro quaternary ammonium compound, wherein the spiro derivative compound obtained in the third step is represented by the chemical formula 6 below:

[Chemical Formula 6]

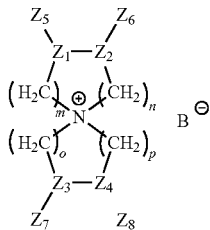

wherein m, n, o, and p are each independently an integer of 0 to 6; $Z_1$, $Z_2$, $Z_3$ and $Z_4$ are each independently CH, $CH_2$, NH, O, or S; $Z_5$, $Z_6$, $Z_7$ and $Z_8$ are each independently $C_1$-$C_6$ alkyl group, $C_1$-$C_5$ alkoxy group, $C_1$-$C_6$ alkenyl group, hydrogen or F; and anion B represents an anion of tetrafluoroborate ($BF_4$), hexafluorophosphate($PF_6^-$) or bis(trifluoromethylsulfonyl)imide(($CF_3SO$)$_2N^-$).

Further, the present invention relates to a method for preparing a spiro quaternary ammonium compound, wherein the resin is used in a molar ratio of 1.0 to 1.3 relative to the cyclic secondary amine derivative.

Further, the present invention relates to a method for preparing a spiro quaternary ammonium compound, wherein the reaction temperature of the first step or the third step is in the range of 80° C. to 90° C.

Further, the present invention relates to a method for preparing a spiro quaternary ammonium compound, wherein the reaction time of the first step is in the range of 6 to 10 hours.

Further, the present invention relates to a method for preparing a spiro quaternary ammonium compound, wherein the reactant of the first step is mixed with one or more compounds selected from the group consisting of acetonitrile, 2-propanol, and tetrahydrofuran.

In addition, the present invention relates to a method for preparing a spiro quaternary ammonium compound, further comprising a step of recycling a resin obtained by reacting the resin obtained in the third step with MA (where M is Li, Na, K, Rb, or Cs; and A represents hydroxide ($OH^-$) or carbonate anion($HCO_3^-$)) obtained in the third step, to the basic resin of the first step.

According to the production method of the present invention, it is possible to produce a spiro quaternary ammonium compound of high purity and to solve the problems of many time and high cost required for purification by a conventional method, thereby producing various spiro quaternary ammonium compounds easily and economically and further allowing the recycling of the basic resin.

DETAILED DESCRIPTION OF THE INVENTION

Hereinafter, the present invention will be described in more detail with reference to Examples. It should be understood that the terms or words used in the specification and the appended claims should not be construed as limited to general and dictionary meanings, but interpreted based on the meanings and concepts conforming to technical aspects of the present invention.

The embodiments described in the present specification are preferred embodiments of the present invention, and do not represent all technical aspects of the present invention, and there may be various equivalents and modifications that can substitute for the embodiments at the time of filing the present application.

[Reaction Scheme 1]

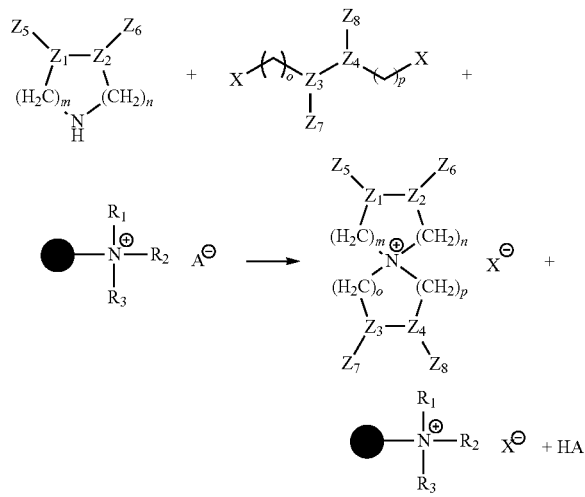

[Reaction Scheme 2]

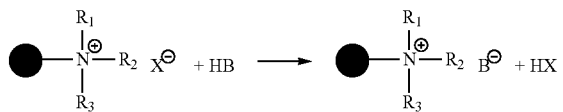

[Reaction Scheme 3]

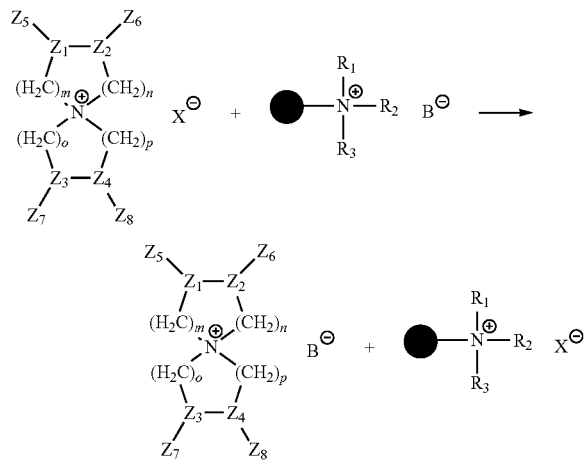

[Reaction Scheme 4]

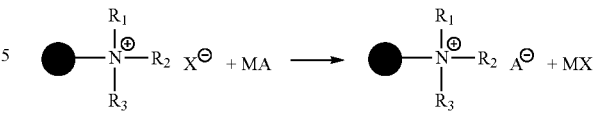

In the reaction scheme 1 through the reaction scheme 4:

m, n, o, and p are each independently an integer of 0 to 6;

$Z_1$, $Z_2$, $Z_3$, and $Z_4$ are each independently CH, $CH_2$, NH, or S;

$Z_5$, $Z_6$, $Z_7$, and $Z_8$ are each independently $C_1$-$C_6$ alkyl group, $C_1$-$C_6$ alkoxy group, $C_1$-$C_6$ alkenyl group, hydrogen or F;

X is Cl, Br, or I;

anion A is a hydroxide ion ($OH^-$) or a carbonate ion ($HCO_3^-$); anion B is an anion of tetrafluoroborate ($BF_4^-$), hexafluorophosphate($PF_6^-$), or bis(trifluoromethylsulfonyl)imide(($CF_3SO_2)_2N^-$);

$R_1$, $R_2$, and $R_3$ are each independently hydrogen or $C_1$-$C_6$ alkyl group; and M is Li, Na, K, Rb, or Cs.

Further, in the reaction scheme 1 through the reaction scheme 4, ●— represents a polymer constituting resin, and ●— polystyrene matrix, styrene-divinylbenzene copolymer, polyacrylic crosslinked divinylbenzne and the like can be used as the polymer. But it is not limited thereto.

In the preparation method of the present invention, the basic resin can be used immediately without any additional purification process. The basic resin used in the preparation method of the present invention is commercially available, and can be selected from, for example, but are not limited to: Amberlite® IRA-743; Dowex® 550A; Purolite® A500MBOHINDPlus, Purolite® A500MBOHPlus, Purolite® A5000HPlus, Purolite® A510MBOHINDPlus, Purolite® A510MBOHPlus, Purofine® PFA4000H, Purofine® PFA6000H, Purolite® A200MBOH, Purolite® A200MBOHIND, Purolite® A300 MB, Purolite® A3000H, Purolite® A400MBOH, Purolite® A400MBOHIND, Purolite® A4000H, Purolite® A600MBOH, Purolite® A600MBOHIND, Purolite® A6000H, Puropack® PPA4000H, and Superge™ SGA5500H, available from Purolite Corporation; LEWATIT® ASB 1 OH, LEWATIT® MonoPlus M 500 OH, LEWATIT® MonoPlus M 800 OH, and LEWATIT® MonoPlus MP 800 OH, available from Lanxess Corporation; Diaion™ SA10AOH (Type I), Diaion™ SA20AOH (Type II), Diaion™ PA312LOH (Type I), Diaionm UBA1200H, Diaion™ UBA1200HUP, and Diaion™ UBA1000HUP (Type I), available from Mitsubishi Chemical Corporation; SBG1P-OH-ID (gel type), SBMP1-OH, SBG1-OH, and SBG2-OH, available from ResinTech, Inc.; Rexinex™ A-4 OH, Rexinex™ A-4 UB OH, Rexinex™ A-7 UB OH, Rexinex™ A-25 OH, Rexinex™ AP OH, and Rexinex™ AP MB OH, available from Jacobi-Resinex Corporation.

In the reaction scheme 1, a cyclic secondary amine derivative can be reacted with dihaloalkane in the presence of a basic resin. In addition, one or a mixture of two or more selected from the group consisting of acetonitrile, 2-propanol, and tetrahydrofuran can be used. In the preferred aspect of the invention, 1,4-dibromobutane is used as the dihaloalkane.

Further, in the synthesis of a spiro compound derivative, based on a molar ratio of 1:1 for a cyclic secondary amine derivative to 1,4-dihalobutane, the basic resin can be used preferably at a molar ratio of 0.9 to 1.5 and more preferably at a molar ratio of 1.0 to 1.3. If the amount of the basic resin used is less than a molar ratio of 1.0, the reaction is not completed. If the amount of the basic resin used is greater than a molar ratio of 1.3, there is a problem that the reaction rate is affected and so the reaction time becomes longer.

In addition, a cyclic secondary amine derivative can be reacted with 1,4-dihalobutane in the presence of a basic resin at a temperatures ranging from 60° C. to 100° C., more preferably from 70° C. to 90° C., and still more preferably from 80° C. to 90° C. If the reaction temperature is less than 80° C., the reaction time becomes longer, and if the reaction temperature is higher than 90° C., there is a problem that the starting material is decomposed and so the yield is lowered.

Further, the cyclic secondary amine derivative can be reacted with 1,4-dihalobutane in the presence of a basic resin within 24 hours. The reaction time may be preferably 2 to 16 hours, more preferably 4 to 14 hours, and still more preferably 6 To 10 hours.

In the reaction scheme 2, the molar ratio of the acid in an aqueous solution may be from 0.9 to 1.3, more preferably from 0.95 to 1.2, still more preferably from 1.0 to 1.1, relative to 1 mole of the resin recovered after being used in the reaction scheme 1. If the molar ratio is less than 1.0, the anion substitution reaction in the reaction scheme 2 is not completed and so the yield is lowered. If the molar ratio is higher than 1.1, there is a problem that the reaction solution changes to acidic.

Further, the acid in the aqueous solution can be reacted with the resin recovered after being used in the reaction scheme 1 at a temperatures from −20° C. to 40° C., more preferably from −10° C. to 30° C. and still more preferably from 0° C. to 25° C.

Further, the acid in the aqueous solution can be reacted with the resin recovered after being used in the reaction scheme 1 within 6 hours. The reaction time may be more preferably from 1 hour to 4 hours and still more preferably from 1 hour to 2 hours.

In the reaction scheme 3, the resin obtained in the reaction scheme 2 can be used at a molar ratio from 0.9 to 1.5, more preferably at a molar ratio from 1.0 to 1.3, relative to 1 mole of the spiro quaternary ammonium derivative compound obtained in the reaction scheme 1. If the resin obtained in the reaction scheme 2 is used at a molar ratio of less than 1.10 relative to 1 mole of the spiro derivative compound obtained in the reaction scheme 1, the reaction is not completed. If the resin is used at a molar ratio of greater than 1.3, there is a problem that it affects a reaction rate and so the reaction time becomes longer.

Further, in the reaction between the spiro derivative compound obtained in the reaction scheme 1 and the resin obtained in the reaction scheme 2, one or a mixture of two or more selected from the group consisting of dichloromethane, acetonitrile, 2-propanol, and tetrahydrofuran can be used.

The reaction between the spiro derivative compound obtained in the reaction scheme 1 and the resin obtained in the reaction scheme 2 can be carried out at a temperature from 60 to 100° C., more preferably from 70 to 90° C., and still more preferably from 80 to 90° C. If the reaction temperature is lower than 80° C., the reaction time becomes longer, and if the reaction temperature is higher than 90° C., there is a problem that the starting material is decomposed and so the yield is lowered.

The reaction between the spiro quaternary ammonium derivative compound obtained in the reaction scheme 1 and the resin obtained in the reaction scheme 2 can be carried out within 12 hours. The reaction time is more preferably between 2 hours and 10 hours, still more preferably between 4 hours and 8 hours, and most preferably between 4 hours and 6 hours.

In the reaction scheme 4, MA may be used at a molar ratio from 0.8 to 1.5, more preferably from 0.9 to 1.3 and still more preferably from 0.95 to 1.1, relative to 1 mole of the resin recovered in the reaction scheme 3. If the molar ratio is less than 0.95, the anion substitution is not completed, and if the molar ratio is higher than 1.1, there is an economical problem.

Further, the reaction between MA and the resin recovered in the reaction scheme 3 can be carried out at temperatures of −20° C. to 40° C. The reaction temperature is more preferably from −10° C. to 40° C., and still more preferably from 0 to 25° C.

In addition, the reaction between MA and the resin recovered in the reaction scheme 3 can be carried out within 12 hours. The reaction time is more preferably from 2 to 8 hours, and still more preferably from 2 to 4 hours.

Further, the resin obtained in the reaction scheme 4 can be reused in the reaction scheme 1, which is advantageous.

EXAMPLES

Example 1: Preparation of Spiro Bipyrrolidinium Bromide 71.1 g (1.0 mol) of pyrrolidine, 215.9 g (1.0 mol) of 1,4-dibromobutane, and 101 g (1.0 mol) of basic resin Amberlite®A26 (1250 ml) were added to 1 L of acetonitrile. The solution was stirred under reflux for 6 hours. After completion of the reaction, the temperature was lowered to room temperature, the resin was filtered, and the acetonitrile solvent was removed to obtain 199.9 g (9'7%) of spirobipyrrolidinium bromide.

Example 2: Preparation of Amberlyst®A26 $BF_4$

Amberlite®A26 Br (125 0 ml) obtained in Example 1 was dissolved in $H_2O$ (5000 ml), the temperature was lowered to 0° C., and 48% aq $HBF_4$ (910 ml) was added. The mixture was stirred for 1 hour, then filtered and dried at room temperature.

Example 3: Preparation of Spiro Bipyrrolidinium Tetrafluoroborate 206.1 g (1.0 mol) of spiro bipyrrolidinium bromide and Amberlite®A26 BF4 (1250 ml) obtained in Example 2 were added and refluxed in acetonitrile (1500 mL) for 4 hours. After completion of the reaction, the temperature was lowered to room temperature, the resin was removed by filtration, and the acetonitrile solvent was removed to obtain 202.4 g (95%) of spirobipyridinium tetrafluoroborate.

Example 4: Preparation of Amberlyst®A26 OH

Amberlite®A26 Br (1250 ml) obtained in Example 3 was added to $H_2O$ (1500 mL), to which 1M NaOH (1000 mL) was added. The mixture was stirred at room temperature for 4 hours, filtered and washed with $H_2O$ (500 mL) and then dried at ambient temperature.

Examples 5-14: Resin Reuse Experiment

The experiments were performed similarly to Examples 1 through 4, and the results are shown in Table 1 below.

TABLE 1

| Example | Number of reuse | Spiro bipyrrolidinium bromide, yield (%) | Spiro bipyrrolidinium tetrafluoroborate, yield (%) |
|---|---|---|---|
| 5 | 1 | 95 | 92 |
| 6 | 2 | 96 | 93 |
| 7 | 3 | 93 | 92 |
| 8 | 4 | 95 | 93 |
| 9 | 5 | 94 | 93 |
| 10 | 6 | 95 | 92 |
| 11 | 7 | 93 | 93 |
| 12 | 8 | 96 | 92 |
| 13 | 9 | 95 | 92 |
| 14 | 10 | 95 | 92 |

Examples 15-17: Preparation of Spiro Bipyrrolidinium Bromide Compound

The title compound was prepared in the same manner as in Example 1, except that the reactions were carried out while changing the molar ratio of the resin, and the results are shown in Table 2 below.

TABLE 2

| Example | Resin/Pyrrolidine (molar ratio) | Yield (%) |
|---|---|---|
| 15 | 0.9 | 70 |
| 16 | 1.3 | 97 |
| 17 | 1.5 | 80 |

Examples 18-20: Preparation of Spiro Bipyrrolidinium Bromide Compound

The title compound was prepared in the same manner as in Example 1, except that the reactions were carried out while changing solvents, and the results are shown in Table 3 below.

TABLE 3

| Example | Solvent | Yield (%) |
|---|---|---|
| 18 | dichloromethane | 50 |
| 19 | 2-propanol | 85 |
| 20 | tetrahydrofuran | 60 |

Examples 21-24: Preparation of Spiro Bipyrrolidinium Bromide Compound

The title compound was prepared in the same manner as in Example 1, except that the reactions were carried out while changing reaction temperatures, and the results are shown in Table 4 below.

TABLE 4

| Example | Reaction Temperature (° C.) | Yield (%) |
|---|---|---|
| 21 | 60 | 85 |
| 22 | 70 | 85 |
| 23 | 90 | 97 |
| 24 | 100 | 60 |

Examples 25-30: Preparation of Spiro Bipyrrolidinium Bromide Compound

The title compound was prepared in the same manner as in Example 1, except that the reactions were carried out while changing the reaction time, and the results are shown in Table 5 below.

TABLE 5

| Example | Reaction Time (h) | Yield (%) |
|---|---|---|
| 25 | 2 | 50 |
| 26 | 4 | 70 |
| 27 | 8 | 97 |
| 28 | 10 | 97 |
| 29 | 14 | 97 |
| 30 | 16 | 97 |

Examples 31-34: Preparation of Resin-$BF_4$ Compound Followed by Preparation of Spiro Bipyrrolidinium Tetrafluoroborate Compound The resin-$BF_4$ compound was prepared in the same manner as in Example 2, except that the reaction was carried out while changing the molar ratio, and then applied to Example 3. The results are shown in Table 6 below.

TABLE 6

| Example | $HBF_4$/Resin (molar ratio) | Yield (%) |
|---|---|---|
| 31 | 0.9 | 85 |
| 32 | 0.95 | 92 |
| 33 | 1.1 | 97 |
| 34 | 1.2 | 97 |

Examples 35-38: Preparation of Resin-$BF_4$ Compound Followed by Preparation of Spiro Bipyrrolidinium Tetrafluoroborate Compound The resin-$BF_4$ compound was prepared in the same manner as in Example 2, except that the reaction was carried out while changing the temperature, and then applied to Example 3. The results are shown in Table 7 below.

TABLE 7

| Example | Reaction Temperature (° C.) | Yield (%) |
|---|---|---|
| 35 | −20 | 95 |
| 36 | −10 | 95 |
| 37 | 25 | 97 |
| 38 | 40 | 90 |

Examples 39-42: Preparation of Resin-$BF_4$ Compound Followed by Preparation of Spiro Bipyrrolidinium Tetrafluoroborate Compound The resin-$BF_4$ compound was prepared in the same manner as in Example 2, except that the reaction was carried out while changing the time, and then applied to Example 3. The results are shown in Table 8 below.

TABLE 8

| Example | Reaction Time (h) | Yield (%) |
|---|---|---|
| 39 | 0.5 | 63 |
| 40 | 2 | 97 |
| 41 | 4 | 95 |
| 42 | 6 | 96 |

Examples 43-45: Preparation of Spiro Bipyrrolidinium Tetrafluoroborate Compound The title compound was prepared in the same manner as in Example 3, except that the reaction was carried out while changing the molar ratio, and the results are shown in Table 9 below.

TABLE 9

| Example | Resin/Spiro bipyrrolidinium bromide (molar ratio) | Yield (%) |
|---|---|---|
| 43 | 0.9 | 85 |
| 44 | 1.3 | 95 |
| 45 | 1.5 | 90 |

Examples 46-48: Preparation of Spiro Bipyrrolidinium Tetrafluoroborate Compound The title compound was prepared in the same manner as in Example 3, except that the reaction was carried out while changing the solvents, and the results are shown in Table 10 below.

TABLE 10

| Example | Solvent | Yield (%) |
|---|---|---|
| 46 | dichloromethane | 40 |
| 47 | 2-propanol | 50 |
| 48 | tetrahydrofuran | 60 |

Examples 49-53: Preparation of Spiro Bipyrrolidinium Tetrafluoroborate Compound The title compound was prepared in the same manner as in Example 3, except that the reaction was carried out while changing the temperature, and the results are shown in Table 11 below.

TABLE 11

| Example | Reaction Temperature (° C.) | Yield (%) |
|---|---|---|
| 49 | 60 | 60 |
| 50 | 70 | 80 |
| 51 | 80 | 95 |
| 52 | 90 | 95 |
| 53 | 100 | 70 |

Examples 54-58: Preparation of Spiro Bipyrrolidinium Tetrafluoroborate Compound The title compound was prepared in the same manner as in Example 3, except that the reaction was carried out while changing the time, and the results are shown in Table 12 below.

TABLE 12

| Examples | Reaction Time (h) | Yield (%) |
|---|---|---|
| 54 | 2 | 80 |
| 55 | 6 | 95 |
| 56 | 8 | 90 |
| 57 | 10 | 85 |
| 58 | 12 | 70 |

Examples 59-62: Preparation of Resin-Anion Compound

The title compound was prepared in the same manner as in Example 4, except that the reaction was carried out while changing the molar ratio, and then applied to Example 1. The results are shown in Table 13 below.

TABLE 13

| Example | NaOH/Resin (Molar Ratio) | Spirobipyrrolidinium bromide yield (%) |
|---|---|---|
| 59 | 0.8 | 80 |
| 60 | 0.9 | 85 |
| 61 | .95 | 94 |
| 62 | 1.1 | 94 |

Examples 63-66: Preparation of Resin-Anion Compound

The title compound was prepared in the same manner as in Example 4, except that the reaction was carried out while changing the reaction temperature, and then applied to Example 1. The results are shown in Table 14 below.

TABLE 14

| Example | Reaction Temperature (° C.) | Spirobipyrrolidinium bromide yield (%) |
|---|---|---|
| 63 | −20 | 93 |
| 64 | −10 | 94 |
| 65 | 25 | 95 |
| 66 | 40 | 90 |

Examples 67-70: Preparation of Resin-Anion Compound

The title compound was prepared in the same manner as in Example 4, except that the reaction was carried out while changing the time, and then applied to Example 1. The results are shown in Table 15 below.

TABLE 15

| Example | Reaction Time (h) | Spirobipyrrolidinium bromide yield (%) |
|---|---|---|
| 67 | 2 | 80 |
| 68 | 6 | 95 |
| 69 | 8 | 95 |
| 70 | 12 | 87 |

What is claimed is:
1. A method for preparing a Spiro quaternary ammonium compound comprising:

a first step of reacting a cyclic secondary amine derivative with dihaloalkane in the presence of a basic ion exchange resin represented by chemical formula 1 below, thereby obtaining a Spiro derivative compound and a resin;

a second step of reacting the resin obtained in the first step with an acid, thereby obtaining a resin represented by chemical formula 2 below; and a third step of reacting the spiro derivative compound obtained in the first step with the resin obtained in the second step thereby obtaining a spiro quaternary ammonium compound and a resin resulting from an ion exchange reaction,

[Chemical Formula 1]

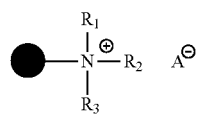

wherein $R_1$, $R_2$ and $R_3$ are each independently hydrogen or $C_1$-$C_6$ alkyl group; anion A represents hydroxide ($OH^-$) or bicarbonate ($HCO_3^-$), and ●— is a polymer constituting resin

[Chemical Formula 2]

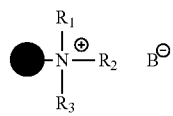

wherein $R_1$, $R_2$, and $R_3$ are each independently hydrogen or $C_1$-$C_6$ alkyl group; anion B represents tetrafluoroborate($BF_4^-$), hexafluorophosphate($PF_6^-$), or bis(trifluoromethylsulfonyl) imide(($CF_3SO_2)_2N^-$), and ●— is a polymer constituting resin.

2. The method for preparing a Spiro quaternary ammonium compound according to claim 1, wherein the cyclic secondary amine derivative of the first step is represented by the chemical formula 3 below:

[Chemical Formula 3]

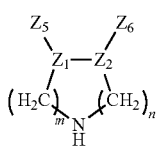

wherein m and n are independently an integer of 0 to 6, $Z_1$ and $Z_2$ is CH, and $Z_5$ and $Z_6$ are each independently $C_1$-$C_6$ alkyl group, $C_1$-$C_6$ alkoxy group, $C_1$-$C_6$ alkenyl group, hydrogen or F.

3. The method for preparing a spiro quaternary ammonium compound according to claim 1, wherein the dihaloalkane of the first step is represented by the chemical formula 4 below:

[Chemical Formula 4]

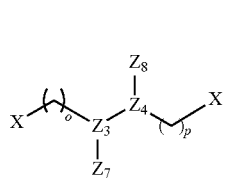

wherein o and p are each independently an integer of 0 to 6;

$Z_3$ and $Z_4$ is CH;

$Z_7$ and $Z_8$ are each independently $C_1$-$C_6$ alkyl group, $C_1$-$C_6$ alkoxy group, $C_1$-$C_6$ alkenyl group, hydrogen or F; and X is Cl, Br, or I.

4. The method for preparing a spiro quaternary ammonium compound according to claim 1, wherein the spiro derivative compound obtained in the first step is represented by the chemical formula 5 below:

[Chemical Formula 5]

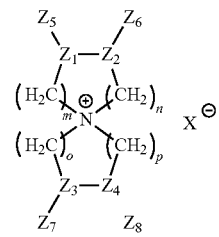

wherein m, n, o, and p are each independently an integer of 0 to 6;

$Z_1$, $Z_2$, $Z_3$ and $Z_4$ is CH;

$Z_5$, $Z_6$, $Z_7$ and $Z_8$ are each independently $C_1$-$C_6$ alkyl group, $C_1$-$C_6$ alkoxy group, $C_1$-$C_6$ alkenyl group, hydrogen or F; and X is Cl, Br, or I.

5. The method for preparing a spiro quaternary ammonium compound according to claim 1, wherein the spiro derivative compound obtained in the third step is represented by the chemical formula 6 below:

[Chemical Formula 6]

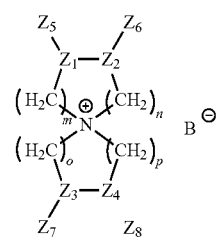

wherein m, n, o, and p are each independently an integer of 0 to 6;

$Z_1$, $Z_2$, $Z_3$ and $Z_4$ is CH;

$Z_5$, $Z_6$, $Z_7$ and $Z_8$ are each independently $C_1$-$C_6$ alkyl group, $C_1$-$C_6$ alkoxy group, $C_1$-$C_6$ alkenyl group, hydrogen or F; and anion B represents an anion of tetrafluoroborate ($BF_4^-$), hexafluorophosphate($PF_6^-$), or bis(trifluoromethylsulfonyl)imide(($CF_3SO_2)_2N^-$).

6. The method for preparing a Spiro quaternary ammonium compound according to claim 1, wherein the basic ion exchange resin is used in a molar ratio of 1.0 to 1.3 relative to the cyclic secondary amine derivative.

7. The method for preparing a spiro quaternary ammonium compound according to claim 1, wherein the reaction temperature of the first step or the third step is in the range of 80 to 90° C.

8. The method for preparing a spiro quaternary ammonium compound according to claim 1, wherein the reaction time of the first step is in the range of 6 to 10 hours.

9. The method for preparing a spiro quaternary ammonium compound according to claim 1, wherein the cyclic secondary amine derivative, the dihaloalkane and the basic ion exchange resin of the first step is mixed with one or more compounds selected from the group consisting of acetonitrile, 2-propanol, and tetrahydrofuran.

10. The method for preparing a spiro quaternary ammonium compound according to claim 1, further comprising a fourth step of regenerating the basic ion resin for reuse in step 1, said fourth step comprising reacting the resin obtained in the third step with MA (where M is Li, Na, K, Rb, or Cs; and A is hydroxide ($OH^-$) or bicarbonate ($HCO_3^-$)), thereby regenerating the basic ion exchange resin of chemical formula 1.

* * * * *